(12) United States Patent
Ye et al.

(10) Patent No.: US 7,236,673 B2
(45) Date of Patent: Jun. 26, 2007

(54) ENHANCING FIBER-OPTIC SENSING TECHNIQUE USING A DUAL-CORE FIBER

(75) Inventors: Jing Yong Ye, Ann Arbor, MI (US); Theodore Norris, Dexter, MI (US); James R. Baker, Jr., Ann Arbor, MI (US); Thomas Thommey, Dexter, MI (US); Mon Myaing, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/372,425

(22) Filed: Mar. 9, 2006

(65) Prior Publication Data

US 2006/0171647 A1    Aug. 3, 2006

Related U.S. Application Data

(62) Division of application No. 10/738,828, filed on Dec. 17, 2003, now Pat. No. 7,046,888.

(60) Provisional application No. 60/434,604, filed on Dec. 18, 2002.

(51) Int. Cl.
*G02B 6/02* (2006.01)

(52) U.S. Cl. .................................. 385/123; 385/12

(58) Field of Classification Search ........ 385/123–128, 385/12
See application file for complete search history.

(56) References Cited

U.S. PATENT DOCUMENTS

| 4,000,416 | A |   | 12/1976 | Goell |
|---|---|---|---|---|
| 4,217,488 | A |   | 8/1980 | Hubbard |
| 4,295,738 | A |   | 10/1981 | Meltz et al. |
| 5,106,193 | A | * | 4/1992 | Fesler et al. ................ 356/460 |
| 5,112,127 | A |   | 5/1992 | Carrabba et al. |
| 5,144,690 | A |   | 9/1992 | Domash |
| 5,963,680 | A | * | 10/1999 | Kleinerman ................. 385/12 |
| 6,411,762 | B1 | * | 6/2002 | Anthon et al. .............. 385/123 |
| 2002/0094528 | A1 |   | 7/2002 | Salafsky |
| 2003/0151000 | A1 |   | 8/2003 | Watanabe et al. |

FOREIGN PATENT DOCUMENTS

EP    1 207 387 A1    11/2000

* cited by examiner

*Primary Examiner*—Ellen E. Kim
(74) *Attorney, Agent, or Firm*—Harness, Dickey & Pierce, P.L.C.

(57) ABSTRACT

An optical fiber for use in fiber optic sensing of a test sample includes a first core and a second core. The second core is generally coaxially disposed within the first core and is sized smaller than the first core. The second core is capable of delivering pulsed laser energy from the laser for nonlinear optical excitation of the test sample. Nonlinear optical feedback signals can then be collected in both the first core and second core for improved detection efficiency relative to conventional single-mode and multi-mode fibers.

7 Claims, 4 Drawing Sheets

ENHANCING FIBER-OPTIC SENSING TECHNIQUE USING A DUAL-CORE FIBER

CROSS-REFERENCE TO RELATED APPLICATIONS

This application is a divisional of U.S. patent application Ser. No. 10/738,828 filed on Dec. 17, 2003, now issued as U.S. Pat. No. 7,046,888, which claims the benefit of U.S. Provisional Application No. 60/434,604, filed on Dec. 18, 2002. The disclosures of the above applications are incorporated herein by reference.

STATEMENT OF GOVERNMENTAL SUPPORT

This invention was made with Government support under Grant No. NOI-CO-97111 awarded by the National Cancer Institute and National Institute of Health. The Government has certain rights in this invention.

FIELD OF THE INVENTION

The present invention relates to fiber optic sensing and, more particularly, to a dual-core fiber for improved detection efficiency relative to conventional single-mode and multi-mode fibers.

BACKGROUND OF THE INVENTION

As is known to those skilled in the art, optical fiber based sensing technology has been rapidly developed and widely used recently in biological and biomedical studies. Many of these studies employ conventional one-photon fluorescence (OPF) measurement techniques. However, there are a number of well-known advantages in using a multiphoton fluorescence including two-photon fluorescence (TPF) measurement technique. The small nonlinear excitation volume in the close proximity of the fiber tip enables local detection at a specific site. The use of near infrared light allows minimization of photodamage to living cells and drugs, in contrast to excitation by energetic UV photons. The large separation in wavelength between two-photon excitation and fluorescence emission facilitates elimination of detection of background noise. Finally, a single laser source may be used to excite a wide variety of fluorophores. Two-photon excitation arises due to the simultaneous absorption of two incident photons by a molecule. This excitation causes a ground-state electron to transition to an excited state of the fluorophore. Because two photons are required for each transition, the probability of excitation is dependent on the square of the instantaneous incident radiation intensity. Thus, an ultra-short-pulsed laser beam is usually needed for efficient excitation.

The recent introduction of optical fibers and fiber-optical components into conventional imaging systems has provided additional advantages. For example, excitation laser beam can be delivered deep into a targeted biological sample through an optical fiber, which otherwise is subject to strong scattering and absorption by biological tissues. In addition, using optical fibers, bulk optics and laser sources may now be placed remotely from the sample to be tested.

However, the use of conventional optical fibers leads to a number of disadvantages due to their physical limitations. Generally, there is a tradeoff between optimal excitation and optimal collection when using a single-mode fiber versus a multi-mode fiber. That is, single-mode fibers create higher laser peak intensity at the exit tip of the optical fiber when compared to multi-mode fibers. This higher laser peak intensity increases the nonlinear optical excitation rate. However, the lower numerical aperture of single-mode fibers suggests that multi-mode fibers have superior collection efficiency of optical signals such as fluorescence.

Accordingly, there exists a need in the relevant art to provide an optical fiber for use with the multiphoton fluorescence measurement technique that is capable of providing high laser peak intensity at the exit tip without compromising the fluorescence collection efficiency. Additionally, there exists a need to provide a dual-core optical fiber for use with two-photon fluorescence measurements that is capable of overcoming the disadvantages of the prior art.

SUMMARY OF THE INVENTION

According to the principles of the present invention, an optical fiber having an advantageous construction and method of fiber optic sensing is provided. The optical fiber includes a first core and a second core. The second core is generally coaxially disposed within the first core and is sized smaller than the first core. The second core is capable of delivering pulsed laser energy from the laser for nonlinear optical excitation of the test sample. Nonlinear optical feedback signals can then be collected in both the first core and second core for improved detection efficiency relative to conventional single-mode and multi-mode fibers.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment is merely exemplary in nature and is in no way intended to limit the invention, its application, or uses.

Figure 1:
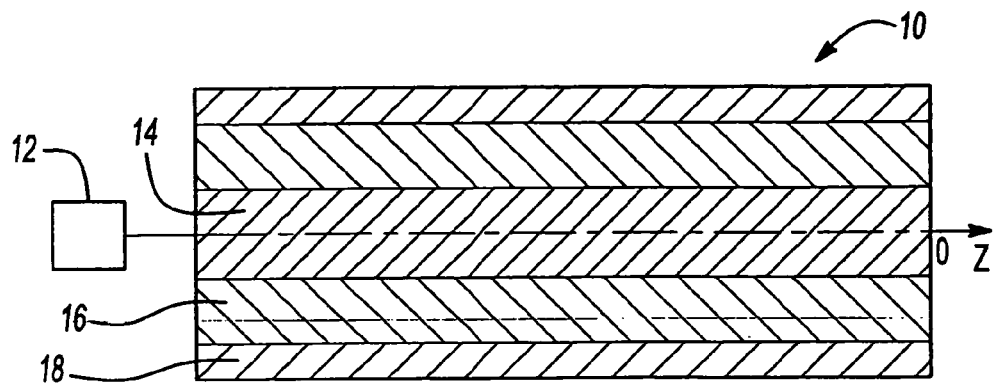
FIG. 1 is a cross-sectional view illustrating a dual-core optical fiber according to the principles of the present invention.
Figure 2:
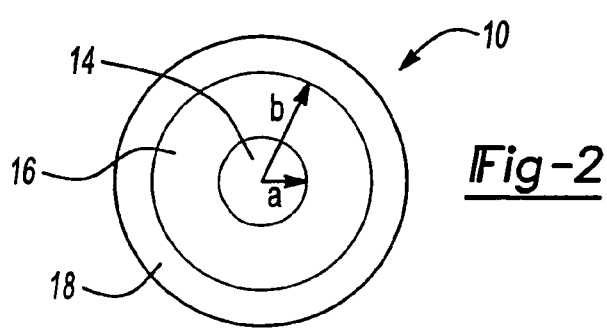
FIG. 2 is an end view illustrating the dual-core optical fiber.

Referring to FIGS. 1 and 2, a dual-core optical fiber, generally indicated at 10, is provided in accordance with the principles of the present invention for use with two-photon fluorescence detection to provide excitation and detection of a specimen through a single optical fiber. That is, dual-core optical fiber 10 permits the optimization of both the excitation rate and collection efficiency in a single optical fiber. A laser source 12 is operably coupled to dual-core optical fiber 10 via conventional means. Laser source 12 may be of any conventional design, such as a general pulsed laser. A detection system (not shown) may include a spectrometer and photon counter. By way of non-limiting example, the laser source used herein was a Ti:sapphire laser providing 80-fs pulses at 830 nm with an 80-MHz repetition rate.

Still referring to FIGS. 1 and 2, dual-core optical fiber 10 is adapted to deliver ultra short laser pulses from laser source 12 through an inner core 14. It should be appreciated that such delivery of ultra short laser pulses, such as about femtosecond pulses, through inner core 14 is similar to single-mode optical fibers, which maintains single-mode propagation which leads to a high nonlinear optical excitation rate. However, dual-core optical fiber 10 further includes an outer core 16 disposed about inner core 14 in a coaxial arrangement to receive or collect two-photon fluorescence. Outer core 16 is surrounded by a cladding 18. As the names imply, outer core 16 has a greater radius B relative to radius A of inner core 14 (FIG. 2). Furthermore, the outer core 16 has a large numerical aperture which ensures high collection efficiency. It has been demonstrated that the total detection sensitivity of dual-core optical fiber 10 is significantly enhanced.

In order to appreciate the trade-off between numerical aperture (NA) and the effects of dispersion in determining the signal level, it is necessary to consider the following. In general, the detected two-photon fluorescence power $P_f$ is given by, $$P_f \propto \int_0^\infty \eta \phi(z) I_{out}^2(z) \tau_{out} R \pi W^2(z) dz \qquad \text{(Eq. 1)}$$

where $\eta$ is the quantum yield of fluorophores, $\Phi(z)$ is the fluorescence collection efficiency determined by the numerical aperture (NA) of the fiber, $I_{out}(z) = CP_L/[R\tau_{out}\pi W^2(z)]$ is the laser peak intensity at a distance z from the fiber tip, C is the fiber coupling efficient, $P_L$ is the average incident laser power, R is the repetition rate of the laser pulses, $\tau_{out}$ is the excitation pulse duration after propagating through the fiber, and W(z) the laser beam radius at position z. For a conventional single-core fiber, either a single-mode fiber or a multi-mode fiber, the analytical solution of Eq. (1) is $$P_f \propto \qquad \text{(Eq. 2)}$$

$$\frac{\eta C^2 P_L^2}{R\tau_{out}\lambda}\left[\arctg\frac{n\lambda}{\pi a(NA)} - \sqrt{1-(NA/n)^2}\arctg\frac{n\lambda\sqrt{1-(NA/n)^2}}{\pi a(NA)}\right]$$

where n is refractive index of the sample, $\lambda$ is the laser wavelength, and a is the radius of the fiber core.

In a single-mode fiber, material dispersion stretches the pulse at the output to $$\tau_{out} = \tau_{in}\sqrt{1+(L/L_D)^2}, \qquad \text{(Eq. 3)}$$

where L is the fiber length, $\tau_{in}$ is the incident pulse duration, and $L_D = \tau_{in}^2/\beta_2$ is the dispersion length with $\beta_2$ representing the dispersion of group velocity.

On the other hand, for a step-index multi-mode fiber, multi-mode distortion is normally much larger than material dispersion, which therefore may be neglected in the following calculation. The broadened pulse duration at the output end of the fiber is given by $$\tau_{out} = n_{core}(NA)^2 L/[cn_{clad}(n_{core}+n_{clad})]. \qquad \text{(Eq. 4)}$$

Figure 3:
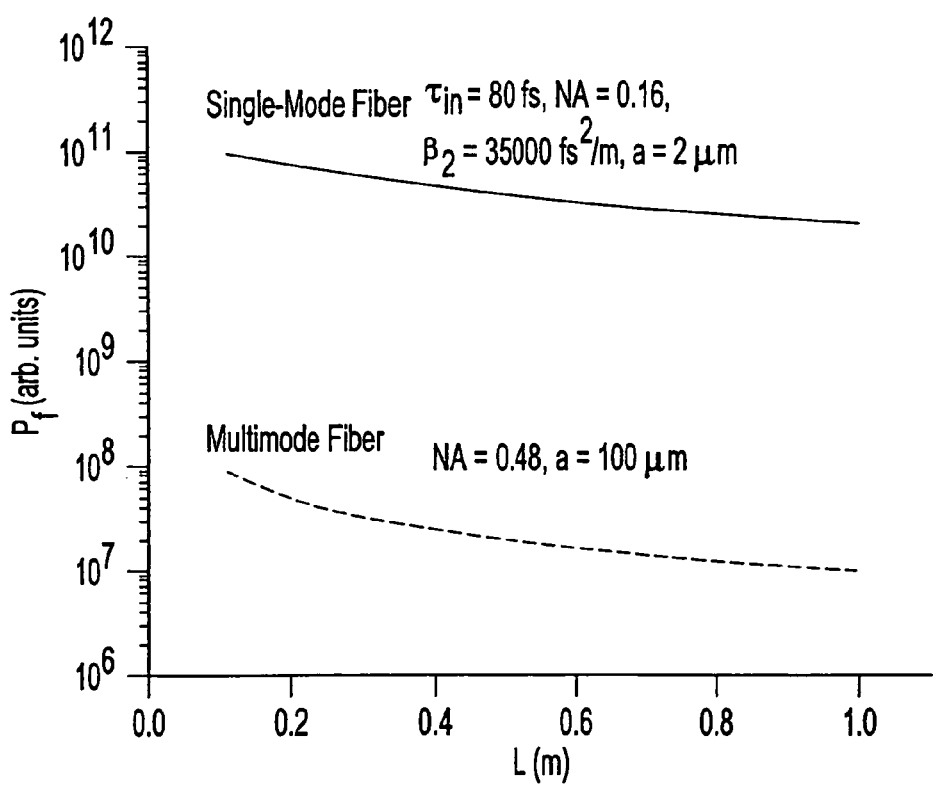
FIG. 3 is a graph showing the calculated result of a two-photon fluorescence detection efficiency comparison between a single-mode fiber and a step-index multimode fiber.

Substituting Eqs. (3) and (4) into Eq. (2), we calculated the relative two-photon fluorescence power detected with a single-mode fiber or a step-index multi-mode fiber. As can be seen in FIG. 3, a single-mode fiber is more efficient than a step-index multi-mode fiber for two-photon fluorescence detection. The reason for this is that the lower collection efficiency (numerical aperture (NA)) of the single-mode fiber is more than offset by the high peak power in the sample.

Figure 4:
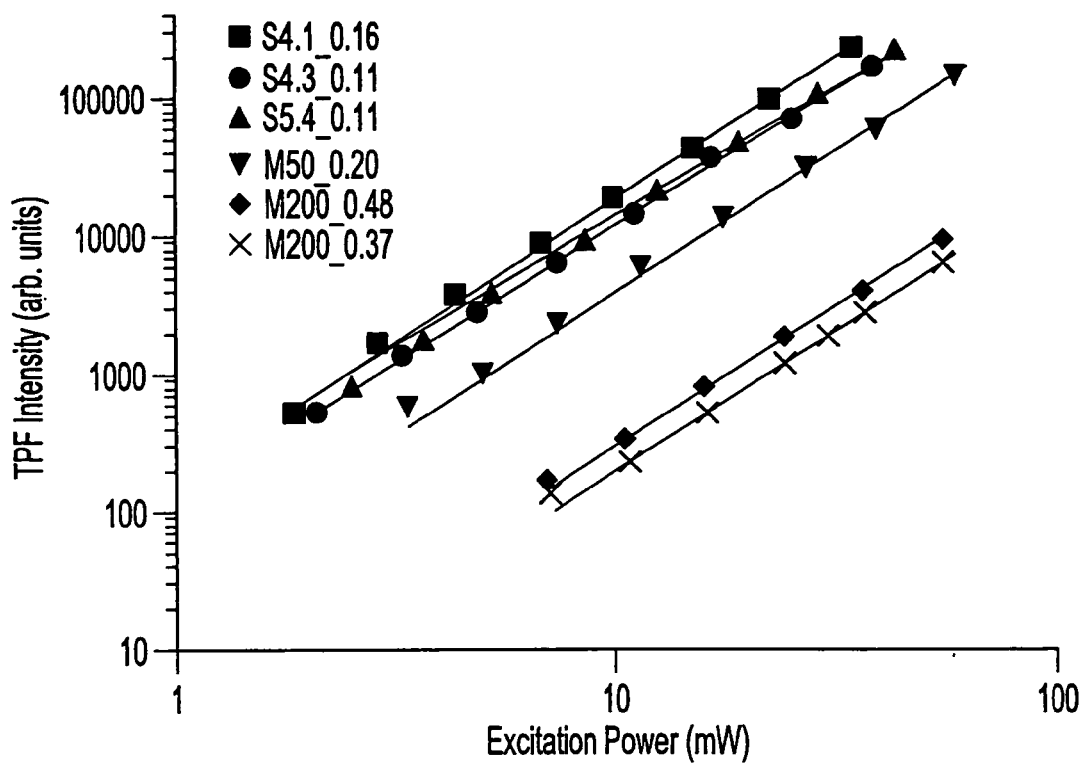
FIG. 4 is a graph illustrating experimental results of two-photon fluorescence detection efficiency using different single- and multi-mode fibers.

This calculated result is qualitatively consistent with the experimental finding illustrated in FIG. 4, although the calculated ratio of the intensity between the single-mode fiber and step-index multi-mode fiber is one order of magnitude higher than that of the experimental result. This difference is understandable because the calculated two-photon fluorescence intensity through a multi-mode fiber is underestimated since Eq. (4) assumes the energy of the excitation pulses is equally distributed to all the available modes. FIG. 4 also shows that a graded-index multi-mode fiber is more efficient in two-photon fluorescence detection than a step-index multi-mode fiber, because of the smaller modal dispersion of the graded-index fibers.

In order to demonstrate that dual core optical fiber 10 is most efficient in two-photon fluorescence detection in comparison with a conventional single-mode fiber or a conventional multi-mode fiber, it is necessary to note the following. For dual core optical fiber 10 having inner core 14 with radius a and outer core 16 with radius b, the collection efficiency $\phi(z)$ is determined by the following equation:

$$\phi(z) = \begin{cases} \frac{1}{2}\left(1-\sqrt{1-(NA_2/n)^2}\right), & \text{for } z \leq \frac{bn}{NA_2}\sqrt{1-(NA_2/n)^2} \\ \frac{1}{2}\left(1-\frac{z}{\sqrt{z^2+b^2}}\right), & \text{for } z > \frac{bn}{NA_2}\sqrt{1-(NA_2/n)^2} \end{cases} \qquad \text{(Eq. 5)}$$

where $NA_2$ is the numerical aperture of outer core 16. Substituting Eq. (5) into Eq. (1), we have analytical solutions of the two-photon fluorescence power $P_f^D$ for a dual-core fiber:

when $\lambda b > \pi a^2$, (Eq. 6)

$$P_f^D \propto \frac{\pi \eta C^2 P_L^2}{4R\tau_{out}\lambda}\left[1 + \frac{a^2}{\sqrt{\lambda^2 b^2 - \pi^2 a^4}}\ln\frac{\lambda bn - NA_2\sqrt{\lambda^2 b^2 - \pi^2 a^4}}{\lambda bn - NA_2\sqrt{\lambda^2 b^2 - \pi^2 a^4}} - \frac{2}{\pi}\sqrt{1 - (NA_2/n)^2}\,\text{arc}tg\frac{\lambda bn\sqrt{1 - (NA_2/n)^2}}{\pi a^2(NA_2)}\right]$$

and when $\lambda b < \pi a^2$ (Eq. 7)

$$P_f^D \propto \frac{\pi \eta C^2 P_L^2}{4R\tau_{out}\lambda}\left[1 - \frac{\pi a^2}{\sqrt{\pi^2 a^4 - \lambda^2 b^2}} + \frac{2a^2}{\sqrt{\pi^2 a^4 - \lambda^2 b^2}}\text{arc}tg\frac{\lambda bn}{(NA_2)\sqrt{\pi^2 a^4 - \lambda^2 b^2}} - \frac{2}{\pi}\sqrt{1 - (NA_2/n)^2}\,\text{arc}tg\frac{\lambda bn\sqrt{1 - (NA_2/n)^2}}{\pi a^2(NA_2)}\right]$$

Figure 5:
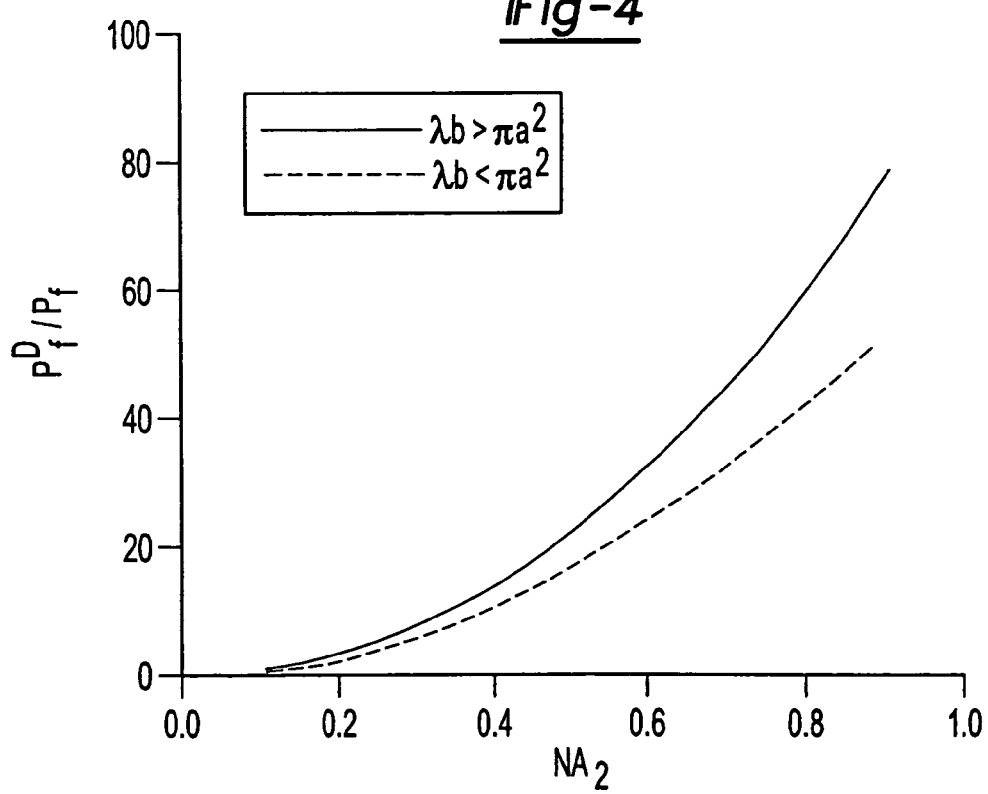
FIG. 5 is a graph illustrating the calculated result of an enhancement factor for a two-photon flourescence signal detected with the dual-core optical fiber.

The ratio between the two-photon fluorescence signal detected through a dual-core fiber and that detected through a conventional single-mode fiber is then calculated. With particular reference to FIG. 5, it can be seen that the two-photon fluorescence signal remarkably increases by using dual-core optical fiber 10 with outer core 16 having a high numerical aperture (NA). For example, assuming inner core 14 has a radius of 2 μm and numerical aperture (NA) of 0.11 as a conventional single-mode fiber, and the refractive index of a sample solution is 1.33, then the enhancement factor is 39-fold for outer core 16 with a radius of 100 μm and numerical aperture (NA) of 0.65. Similarly, the enhancement factor in connection with the present invention is 29-fold when outer core 16 has a radius of 15 μm and a numerical aperture (NA) of 0.65. This enhanced two-photon fluorescence signal allows one to significantly increase detection sensitivity, which is very important in many applications, such as biosensing of extremely low concentration of fluorescent probe molecules in tissues.

Figure 6:
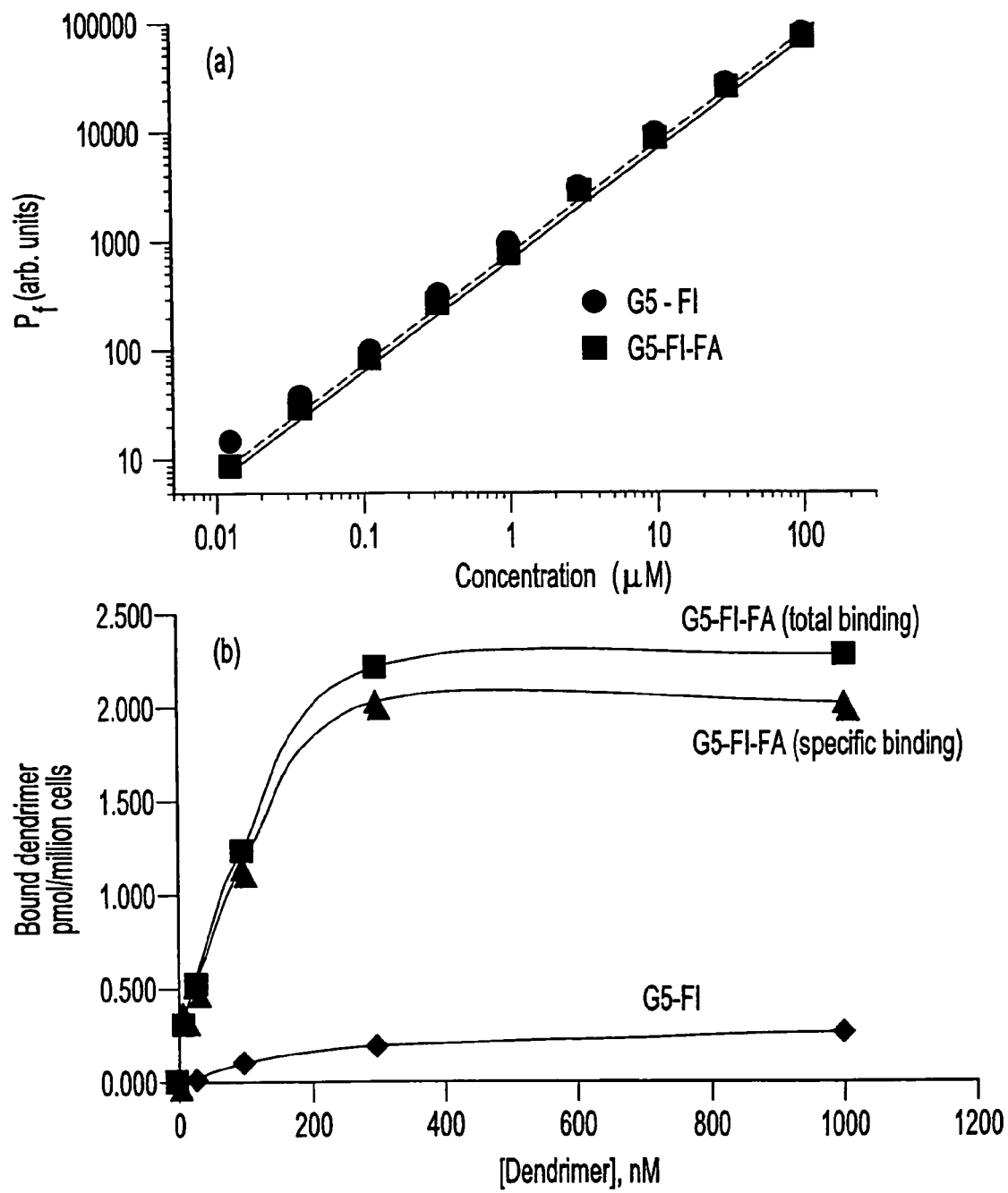
FIG. 6a is a graph illustrating two-photon flourescence power as a function of the concentrations of G5-FI and G5-FI-FA.
FIG. 6b is a graph illustrating a dose-response curve for the binding of G5-FI and G5-FI-FA on KB cells.

In an attempt to demonstrate the utility of the present invention, the following sets forth experimental results of the fiber-optic sensing technique of the present invention based on two-photon fluorescence detection. The present invention was successfully in biosensing the uptake of a targeted dendrimer-based drug delivery agent into cultured KB cells (a sub-line derived from the cervical carcinoma HeLa cell line). The generation 5 dendrimers (G5) used are conjugated both to a fluorescent dye; fluorescein isothiocyanate (FI), for optical sensing of the presence of dendrimers in the cells; and to folic acid (FA), which enables the dendrimers to be selectively taken up by FA-receptor-positive KB cells. The binding of G5-FI-FA and control G5-FI dendrimer to KB cells was then investigated. First, the two-photon fluorescence of standard solutions of G5-FI and G5-FI-FA in the absence of KB cells was measured and exhibited the expected linear concentration dependence as seen in FIG. 6a. The two-photon fluorescence power from cultured KB cell pellets treated with different concentrations of dendrimer solution was then measured. The measured fluorescence was used to determine quantitatively the number of dendrimer molecules bound to the KB cells. As seen in FIG. 6b, the binding as a function of the concentration used to treat the cells is illustrated. The total G5-FI-FA bound to the KB cells is significantly higher than that for G5-FI, which is expected since the G5-FI is taken into the cells non-specifically. Both the binding parameters and the saturation kinetics are consistent with previous flow cytometric data. Thus, the fiber-based biosensing technique appears to be a viable method for real-time in vivo monitoring of uptake of drugs into tumors.

Figure 7:
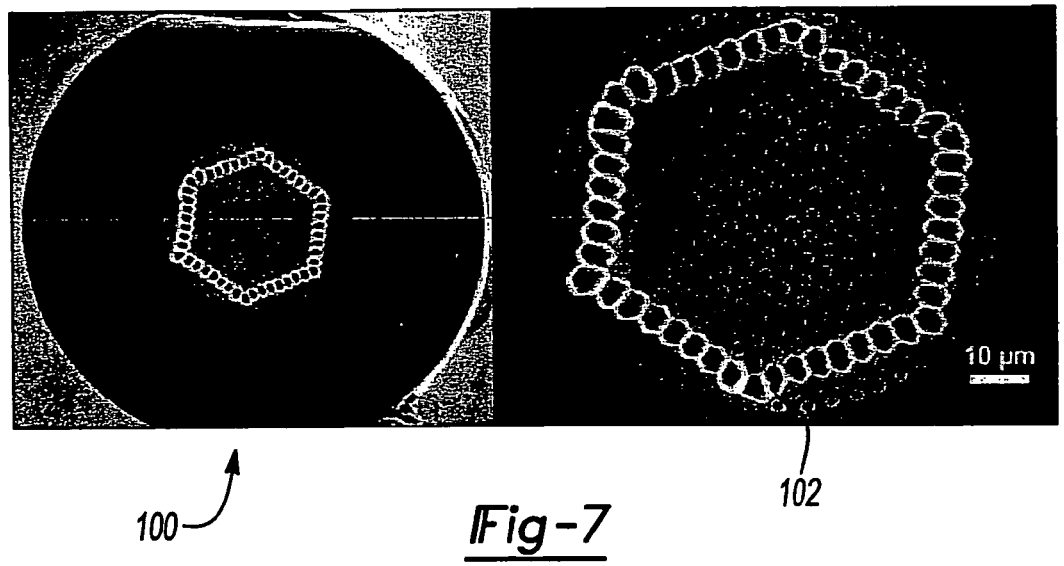
FIG. 7 is an SEM of a dual-core photonic crystal fiber according to the present invention.

As seen in FIG. 7, a dual-core photonic crystal fiber (DCPCF) 100 is provided according to the present invention. Dual-core photonic crystal fiber 100 is just one example of a dual-core fiber. Dual-core photonic crystal fiber 100 is designed to ensure endlessly single mode guidance down the centrally situated core 102. The photonic crystal structure with smaller air holes surrounding the center core is surrounded by a silica web with larger air holes. Thus, the PC structure with small air holes acts as an outer core with a very high NA in contrast to the inner solid core. This allows single mode two-photon excitation and multimode collection of two-photon fluorescence.

Figure 8:
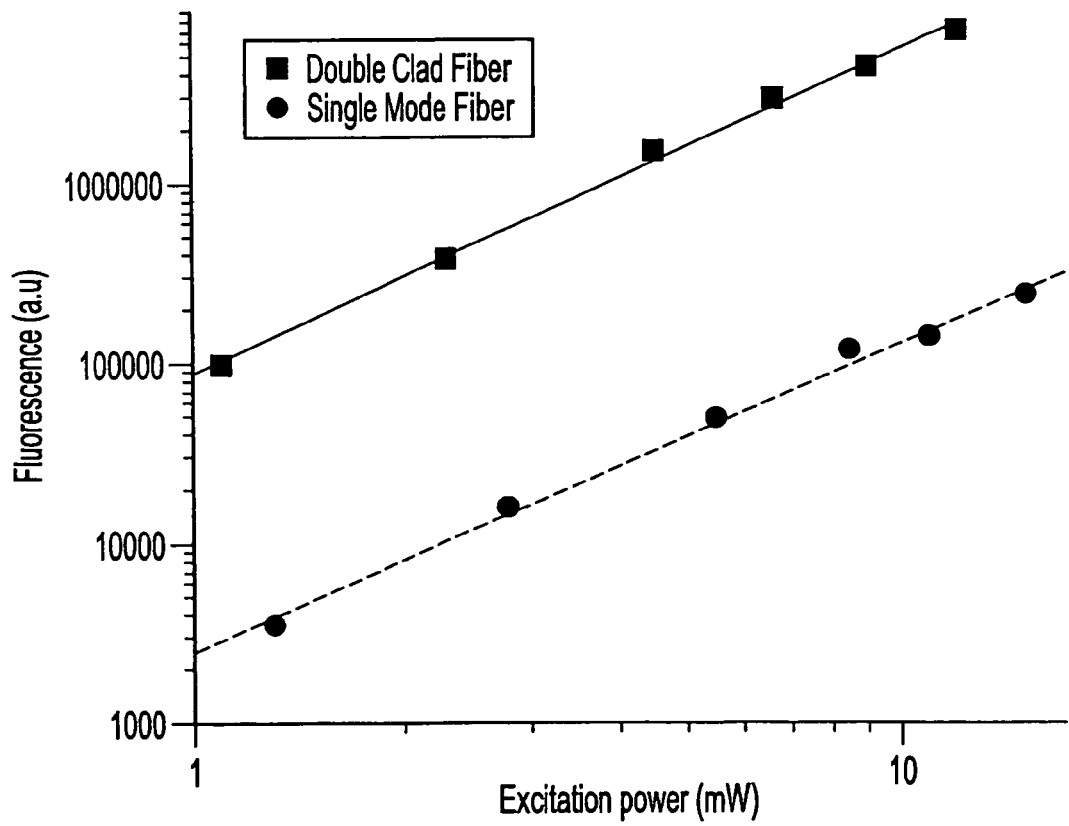
FIG. 8 is a graph illustrating two-photon flourescence using a dual-core photonic crystal fiber and a single mode fiber.

Using Rhodamine 6G gel as a sample, a comparison study of two-photon fluorescence excitation and detection with a single mode fiber and dual-core photonic crystal fiber 100 was performed. As a result of the outer core, dual-core photonic crystal fiber 100 can also support propagating modes—the light that would otherwise be lost in a regular cladding region of the single mode fiber. By spatial filtering, it was found that about 40% of the output excitation light of the DCPCF is in the inner core. FIG. 8 illustrates that for equal average excitation power in the single mode core, the present invention achieves an enhancement of over 30 times in the level of detected fluorescence. Two-photon fluorescence excited by light in the outer core of the fiber was two orders of magnitude less than that excited by the light in the inner core, thereby justifying the comparison as a function of average power in the inner core. This significant improvement in two-photon fluorescence detection using a dual-core photonic crystal fiber 100 suggests the application of this fiber 10 to in vivo biosensing with notably enhanced sensitivity.

This dual-core fiber can be coupled with a lens, such as a Gradient Index (GRIN) lens, to focus excitation light into a test sample. The excitation light then excites flourescence from the test sample. The collected fluorescence with the lens normally forms a bigger spot (or a defocused flourescence arrangement) than the excitation beam at the fiber tip due to chromatic aberration (CA). However, due to the dual-core structure of the present invention, the fluorescence (even that being defocused through CA) can still enter the outer core, thus ensuring high collection efficiency. This feature is another advantage of a dual-core fiber over a single-mode fiber; the amount of fluorescence collected into single-mode fiber will be very small, making the single-mode fiber essentially useless in this application, whereas almost all the fluorescence can be collected into the dual-core fiber.

In sum, it is known that in a conventional fiber, light is guided in a high-index-of-refraction region called the core, and the core is surrounded by a lower-effective-index-of-refraction region called the cladding. There are two kinds of conventional fibers, i.e., single-mode and multimode fibers. They had been the standard technology for many years, and a wide variety of these fibers are commercially available. It has been found that there is a tradeoff between optimal excitation and optimal collection when using a single mode versus a multimode fiber. To solve this problem, by way of the present invention, it has been determined that by using a dual-core fiber the excitation light from the laser will be guided down a central core which is essentially similar to a standard single-mode fiber propagation. However, this central core is surrounded by a second core and an outer cladding layer. This structure enables the second core to support multimode propagation; thus the collection efficiency of fluorescence back through the fiber is higher than that in a conventional single-mode fiber. Through the use of the dual-core fiber of the present invention, one can take advantage of the merits of both a single mode and a multimode fibers at the same time, such as high efficiency of nonlinear optical excitation and high fluorescence collection, while simultaneously avoiding the drawbacks of each, such as low collection efficiency of single mode fibers and inefficiency of nonlinear optical excitation with multimode fibers.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for sensing of a test sample, comprising: an optical fiber and a source of pulsed light energy directed to said optical fiber, wherein said optical fiber comprises:
    a first core;
    a second core generally coaxially disposed within said first core, said second core being sized smaller than said first core, said second core capable of receiving the pulsed light energy from the source for nonlinear optical excitation of the test sample; and
    a detector for collecting fluorescence signals having a spectrometer and a photon counter whereby the fluorescence signals are transmitted to said detector from said test sample.

2. The system according to claim 1 wherein said first core has a first radius and said second core has a second radius, said first radius being greater than said second radius.

3. The system according to claim 2 wherein said first core has a numerical aperture larger than that of said second core.

4. The system according to claim 1 wherein said nonlinear optical excitation comprises two-photon excitation signals.

5. The system according to claim 4 wherein said fluorescence signals comprise two-photon fluorescence signals.

6. A system for sensing of a test sample selected from the group consisting of biologic, organic and combinations thereof comprising: a test sample, an optical fiber and a source of pulsed light energy directed to said optical fiber, wherein said optical fiber comprises:
    a first core;
    a second core generally coaxially disposed within said first core, said second core being sized smaller than said first core, said second core capable of receiving the pulsed light energy from the source for nonlinear optical excitation of the test sample; and
    a detector for collecting fluorescence signals having a spectrometer and a photon counter whereby the fluorescence signals are transmitted to said detector from said test sample.

7. The system according to claim 6 wherein said optical feedback signals comprise fluorescence, luminescence, phosphorescence and combinations thereof.

* * * * *